(12) United States Patent
Grafton et al.

(10) Patent No.: US 6,569,188 B2
(45) Date of Patent: *May 27, 2003

(54) HEX DRIVE BIOABSORBABLE TISSUE ANCHOR

(75) Inventors: R. Donald Grafton, Naples, FL (US); Mark Brunsvold, Naples, FL (US)

(73) Assignee: Arthrex, Inc., Naples, FL (US)

(*) Notice: Subject to any disclaimer, the term of this patent is extended or adjusted under 35 U.S.C. 154(b) by 5 days.

This patent is subject to a terminal disclaimer.

(21) Appl. No.: 09/882,057

(22) Filed: Jun. 18, 2001

(65) Prior Publication Data

US 2002/0022862 A1 Feb. 21, 2002

Related U.S. Application Data

(63) Continuation-in-part of application No. 09/469,177, filed on Dec. 21, 1999, now Pat. No. 6,319,270, and a continuation-in-part of application No. 08/954,206, filed on Oct. 20, 1997, now Pat. No. 6,214,031, which is a continuation of application No. 08/905,393, filed on Aug. 4, 1997, now abandoned.

(60) Provisional application No. 60/118,788, filed on Feb. 4, 1999, provisional application No. 60/023,011, filed on Aug. 5, 1996, and provisional application No. 60/212,830, filed on Jun. 21, 2000.

(51) Int. Cl.[7] ............................................... A61B 17/04
(52) U.S. Cl. ...................................................... 606/232
(58) Field of Search ....................... 606/73, 232, 72, 606/77; 81/436, 461, 437, 52, 57.42, 58.2, 460, 58, 439; 30/173; 411/403, 405, 919

(56) References Cited

U.S. PATENT DOCUMENTS

| 1,088,046 | A | | 2/1914 | Turner | |
|---|---|---|---|---|---|
| 1,300,275 | A | * | 4/1919 | Johnson | ........................ 81/120 |
| 2,347,567 | A | * | 4/1944 | Kreese | ........................ 424/487 |
| 4,175,555 | A | | 11/1979 | Herbert | |
| 4,289,124 | A | | 9/1981 | Zickel | |
| 4,537,185 | A | | 8/1985 | Stednitz | |
| 4,632,100 | A | | 12/1986 | Somers et al. | |
| 4,976,715 | A | | 12/1990 | Bays et al. | |
| 5,061,181 | A | | 10/1991 | Niznick | |
| 5,067,956 | A | | 11/1991 | Buford, III et al. | |
| 5,100,417 | A | | 3/1992 | Cerier et al. | |
| 5,152,790 | A | | 10/1992 | Rosenberg et al. | |
| 5,156,616 | A | | 10/1992 | Meadows et al. | |
| 5,169,400 | A | | 12/1992 | Mühling et al. | |
| 5,180,382 | A | | 1/1993 | Frigg et al. | |

(List continued on next page.)

FOREIGN PATENT DOCUMENTS

| EP | 0611557 | 8/1994 |
|---|---|---|
| EP | 0663184 | 7/1995 |
| EP | 0686373 | 12/1995 |
| FR | 2671717 | 7/1992 |
| WO | 9321848 | 11/1993 |

OTHER PUBLICATIONS

Mitek brochure, Fastin ® RC Dual-Channeled Anchor, Mitek Products, Westwood MA (1999).
Arthrex brochure, "Corkscrew™ Suture Anchors," Arthrex, Inc., Naples, FL (1996).

Primary Examiner—Eduardo C. Robert
(74) Attorney, Agent, or Firm—Dickstein Shapiro Morin & Oshinsky, LLP

(57) ABSTRACT

A headed bioabsorbable tissue anchor has a continuous thread spiraling around a tapering central core. At the distal end, the headed bioabsorbable tissue anchor terminates in a flat point. At the proximal end, the bioabsorbable tissue anchor has a flat, disk-shaped head for engaging tissue, and slots formed in the head for engaging a driver. The anchor also has a cannula shaped to engage the driver. The headed bioabsorbable tissue anchor has a large thread surface per turn of thread. As the anchor is turned into bone for engaging cancellous bone, the disk-shaped head engages and anchors the tissue to the bone.

12 Claims, 6 Drawing Sheets

U.S. PATENT DOCUMENTS

| | | | |
|---|---|---|---|
| 5,246,441 A | * 9/1993 | Ross et al. | 606/53 |
| 5,261,914 A | 11/1993 | Warren | |
| 5,366,330 A | 11/1994 | Cosenza | |
| 5,370,662 A | 12/1994 | Stone et al. | |
| 5,417,533 A | 5/1995 | Lasner | |
| 5,443,482 A | 8/1995 | Stone et al. | |
| 5,522,843 A | 6/1996 | Zang | |
| 5,573,548 A | 11/1996 | Nazre et al. | |
| 5,584,836 A | 12/1996 | Ballintyn et al. | |
| 5,607,432 A | 3/1997 | Fucci | |
| 5,643,269 A | 7/1997 | Härle | |
| D385,352 S | 10/1997 | Bales et al. | |
| 5,683,401 A | 11/1997 | Schmieding et al. | |
| 5,697,950 A | 12/1997 | Fucci et al. | |
| 5,720,766 A | 2/1998 | Zang et al. | |
| 4,237,754 A | 4/1998 | Battrick | |
| 5,575,602 A | 4/1998 | Savage et al. | |
| 5,738,685 A | 4/1998 | Halm et al. | |
| 5,743,914 A | * 4/1998 | Skiba | 606/73 |
| 5,827,291 A | 10/1998 | Fucci et al. | |
| 5,840,078 A | 11/1998 | Yerys | |
| 5,968,047 A | * 10/1999 | Reed | 606/76 |
| 6,077,267 A | * 6/2000 | Huene | 606/73 |
| 6,096,060 A | 8/2000 | Fitts et al. | |
| 6,319,270 B1 | * 11/2001 | Grafton et al. | 606/232 |

* cited by examiner

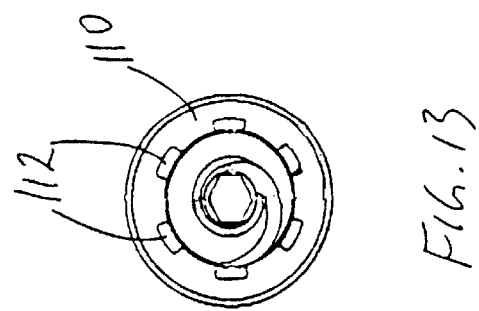
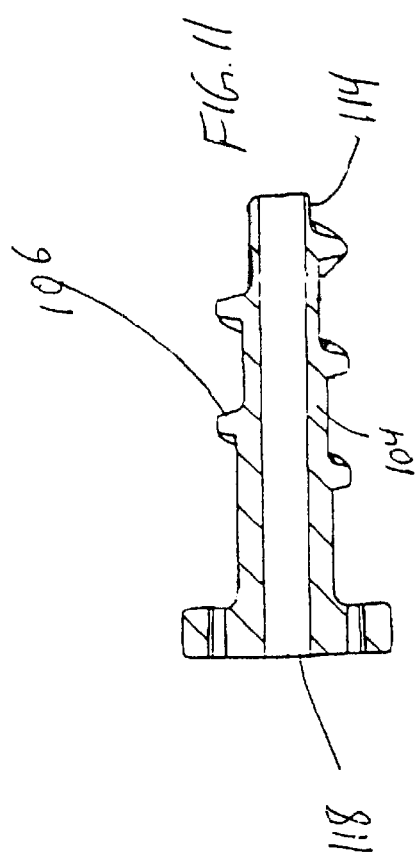
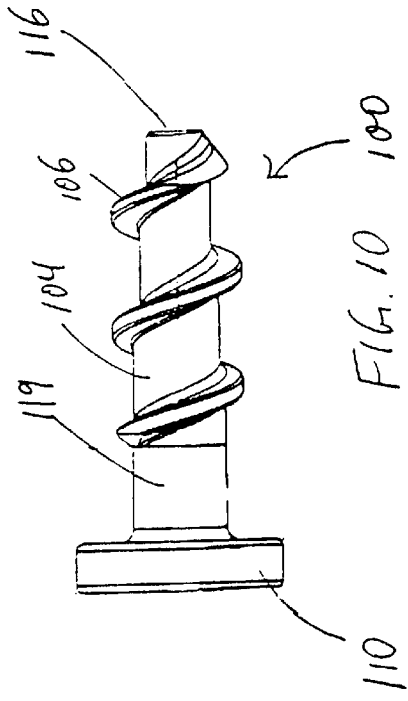
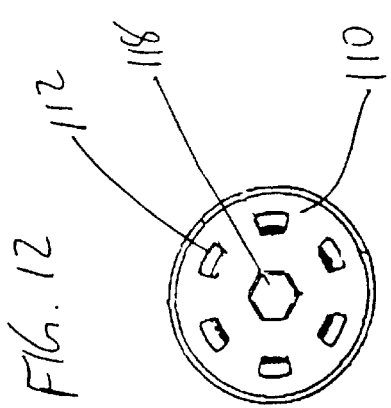

HEX DRIVE BIOABSORBABLE TISSUE ANCHOR

This application is a continuation-in-part of U.S. application Ser. No. 09/469,177, filed Dec. 21, 1999, now U.S. Pat. No. 6,319,270, which claims the benefit of U.S. Provisional Application No. 60/118,788, filed Feb. 4, 1999, and is a continuation-in-part of U.S. application Ser. No. 08/954,206, filed Oct. 20, 1997, now U.S. Pat. No. 6,214,031, which is a continuation of U.S. application Ser. No. 08/905,393, filed Aug. 4, 1997, now abandoned, which claims the benefit of U.S. Provisional Application No. 60/023,011, filed Aug. 5, 1996. This application also claims the benefit of U.S. Provisional Application No. 60/212,830, filed Jun. 21, 2000.

BACKGROUND OF THE INVENTION

1. Field of the Invention

The present invention relates to an apparatus and method for fixation of soft tissue to bone. More specifically, the present invention relates to sutureless arthroscopic apparatus and methods for anchoring soft tissue to bone using a headed bio-absorbable tissue anchor.

2. Description of the Related Art

When soft tissue tears away from bone, reattachment becomes necessary. Various fixation devices, including sutures, screws, staples, wedges, and plugs have been used in the past to secure soft tissue to bone. More recently, various types of threaded suture anchors have been developed.

The known suture anchors generally require that the surgeon tie knots in the suture to secure tissue to the bone. Tying surgical knots is tedious and time-consuming. It would be preferable to be able to secure the soft tissue to the bone in one step without having to tie knots.

Accordingly, a need exists for a bioabsorbable anchor for soft tissue fixation that can be installed to secure tissue easily and effectively without sutures. A need also exists for a soft tissue fixation device that displaces a minimum amount of bone upon insertion. In addition, a need exists for a tissue fixation device having exceptional pull-out strength, especially in soft bone.

SUMMARY OF THE INVENTION

The present invention overcomes disadvantages of the prior art, such as those noted above, by providing a headed bioabsorbable tissue anchor having a thread spiraling helically around a central body, in which the head of the anchor engages the soft tissue for fixation to bone.

The headed bioabsorbable tissue anchor of the present invention has a cannulated, threaded central body. A flat, disk-shaped head is provided on the proximal end of the anchor. The disk-shaped head engages soft tissue for fixation as the anchor is installed through soft tissue and into bone.

The central body of the anchor tapers toward the distal end. The distal tip preferably is flat to avoid tip breakage, as could occur with a pointed tip.

The anchor is formed of a bioabsorbable PLA copolymer, preferably poly (L/D-lactide) acid.

Surgical installation is achieved using a driver that engages the disk-shaped head for installing the threaded anchor by turning into the bone. The anchor head has at least one opening for engagement with the end of a driver. In addition, the driver engages the cannula of the anchor.

The outer circumferential dimension of the disk-shaped head advantageously is substantially larger than the circumference of the central body. Accordingly, the enlarged head engages tissue and holds it in place against the bone into which the tissue anchor has been installed.

Advantageously, the threads of the headed bioabsorbable tissue anchor of the present invention have a cancellous thread design that provides an increased percentage of thread surface area for each turn of the anchor, as compared with known anchors, thus providing increased pull-out strength, and a decreased tendency for back-out. The cancellous thread design is similar to the metal suture anchor described in U.S. Pat. No. 6,214,031, the entire disclosure of which is incorporated herein by reference.

In addition to increased pull-out strength, the one piece sutureless design of the implant advantageously eliminates suture management issues, and simplifies the arthroscopic surgical technique. Further, revisions are simplified, and the biocompatible PLA copolymer material will not interfere with MRI or CT scans. The wide, low profile head provides a broad area of tissue to bone contact without impingement on other tissues. Also, the cannulated design allows the use of a guide wire to ensure accurate implant placement. The implant also can be used in open procedures.

Other features and advantages of the present invention will become apparent from the following description of the invention, which refers to the accompanying drawings.

BRIEF DESCRIPTION OF THE DRAWINGS

FIG. 10 is an elevation of an alternative embodiment of the headed bioabsorbable tissue anchor according to the present invention.

FIG. 11 is a cut-away elevation of the headed bioabsorbable tissue anchor of FIG. 10.

FIG. 12 is a proximal end view of the tissue anchor of FIG. 10.

FIG. 13 is a distal end view of the tissue anchor of FIG. 10.

DETAILED DESCRIPTION OF THE PREFERRED EMBODIMENTS

Figure 1:
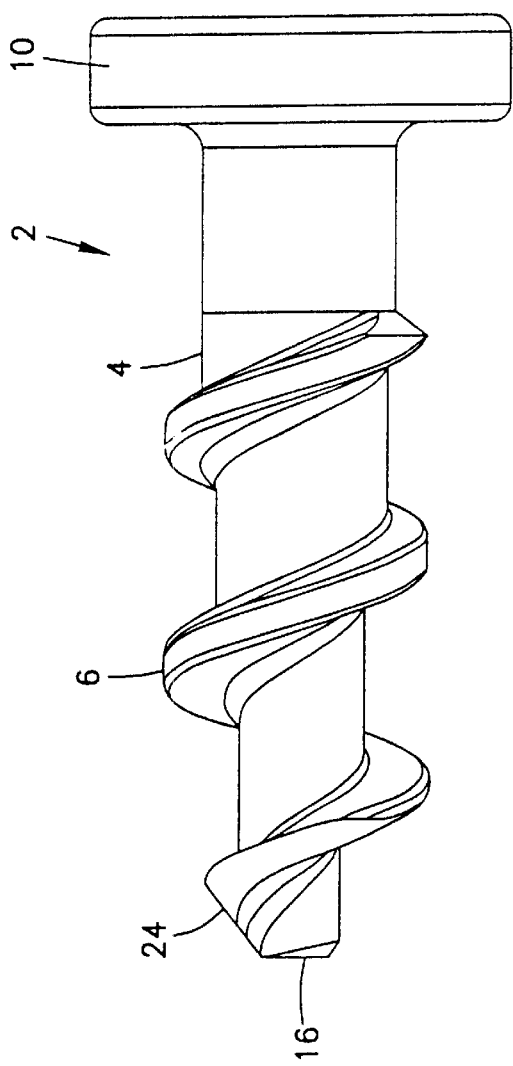
FIG. 1 is a side elevation of a headed bioabsorbable tissue anchor according to the present invention.
Figure 2:
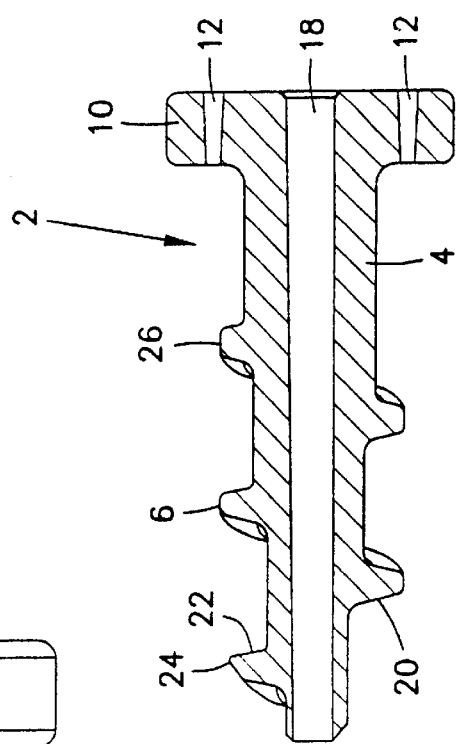
FIG. 2 is a cut-away side elevation of the headed bioabsorbable tissue anchor if FIG. 1.
Figure 3:
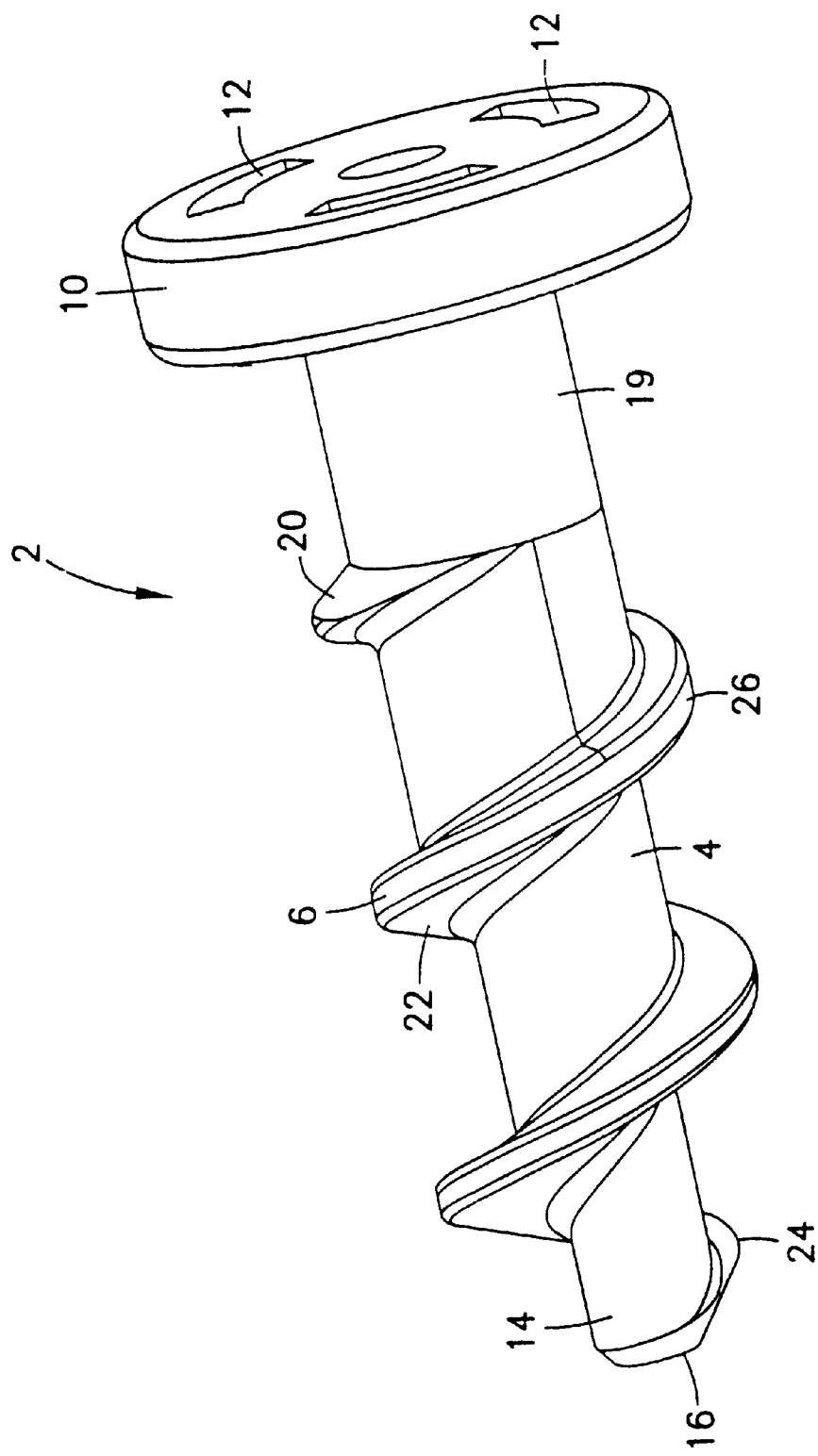
FIG. 3 is a perspective view of the headed bioabsorbable tissue anchor of FIG. 1.

Referring to FIGS. 1–3, the headed bioabsorbable tissue anchor 2 of the present invention includes a body 4 provided in the shape of a cannulated, tapered cylinder. A continuous thread 6 wraps around body 4 in a clockwise direction, as shown. The thread preferably has an outer diameter of 5.0 mm. The outer diameter of the thread remains substantially constant, while the inner diameter of the thread decreases distally, following the taper of the body 4. Accordingly, the surface area of the thread increases distally. The central core of body 4 preferably is circular in cross-section, and tapers from a maximum diameter near the proximal end to a minimum diameter toward the distal end.

Headed bioabsorbable tissue anchor 2 is provided at the proximal end of body 4 with a head 10. The anchor is provided with at least one opening for engaging a driver. Although many different drive coupling arrangements are possible, in the preferred embodiment of the invention, equally spaced arcuate slots 12 are formed in the disk-shaped head to engage the driver described more fully below. The driver is used for delivery and installation of the anchor. Slots 12 formed in the head of the anchor preferably taper to enhance retention of the anchor on the distal end of the driver. The head 10 is 8.0 mm in diameter to provide a broad area of tissue-to-bone contact, and has a smooth, low 1.5 mm thick profile to minimize trauma to surrounding tissue.

At the distal tip 14, the anchor terminates in a flat end 16. The flat end is less likely than a pointed tip to break off and become a loose body within the patient. Cannula 18 is provided centrally. Preferably, the cannula has a circular cross-section; however, the cannula could be shaped to engage a driver for installation of the anchor by turning. Accordingly, the cannula could be hexagonal or provided with ridges, for example.

The head 10 preferably is separated from the thread 6 by a smooth section 19 that passes through and accommodates the tissue atraumatically upon insertion of the anchor into bone, as described more fully below.

The anchor preferably is formed of a bioabsorbable, biocompatible material. Preferably, the anchor material is a PLA copolymer, most preferably poly(L/D-lactide) acid (PLDLA) having a high inherent viscosity.

Anchor thread 6 has a proximal face 20, a distal face 22 and an edge. Near distal tip 14, the edge is formed at an acute angle to the proximal face so as to provide a V-shaped edge 24 that provides a better purchase on the bone as the anchor is advanced by turning during installation. Proceeding proximally along the anchor thread, the thread widens toward a U-shape and the edge becomes substantially parallel with the central axis of the anchor to provide a flat edge 26. The thickness of the thread 6 increases, preferably continuously, from the distal end to the proximal end, as the profile of the edge changes from the sharp V edge 24 to the increasingly wider flat edge 26. The overall configuration provides a spiral wedge that enhances fixation.

Preferably, between two and three flights or turns of thread 6 are provided along body 4, between the proximal end and the distal tip. Adjacent sections of each flight are separated by a gap that is determined by the number of turns per inch of the thread.

Increased surface area of the thread also is achieved in part by providing an increased ratio of the outer diameter of the thread to the inner diameter of the thread along at least a portion of the anchor. Preferably, the ratio is between 2.25 and 2.75. Most preferably, the ratio of the outer diameter to the inner diameter is at least 2.5 along at least a portion of the thread.

In addition, the headed bioabsorbable tissue anchor has a higher thread pitch than prior art screws, thus increasing the area of thread for each turn of the screw, which leads also to greater pull-out strength and faster installation. Significantly, due to the increased pitch, fewer turns are required to advance the headed bioabsorbable tissue anchor into position during installation of the device. Accordingly, the headed bioabsorbable tissue anchor is easy to install, and displaces less tissue material upon insertion than known anchors.

The pull-out strength and minimal tissue damage are enhanced by the relatively compressed cross-sectional aspect of the thread, particularly in relation to the broad axial faces of the threads. Further, in contrast to the tapered central axis, the threads maintain a substantially fixed outer diameter along their length.

Increased back-out resistance can be enhanced further by surface features, such as indentations or radial ridges, on the top and/or bottom faces of the screw threads. The surface features augment the engagement between the thread surfaces and the surrounding tissue once the headed bioabsorbable corkscrew is installed.

Figure 4:
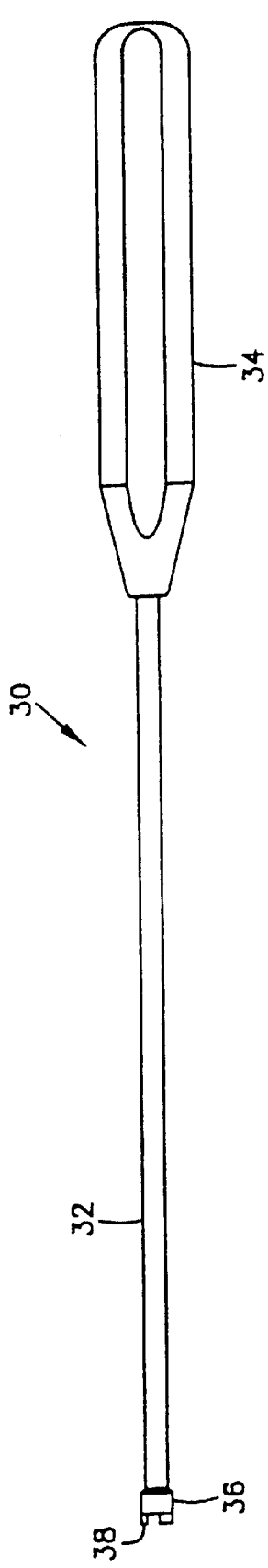
FIG. 4 is an elevation of a driver according to the present invention.

FIG. 4 illustrates a preferred headed bioabsorbable tissue anchor driver 30 according to the present invention. The driver 30 has a cannulated shaft 32 attached to a cannulated handle 34. At the distal end of shaft 32 a head 36 includes three arcuate projections 38 which engage the tapered, arcuate slots 12 formed in the head of the screw 2.

Figure 5:
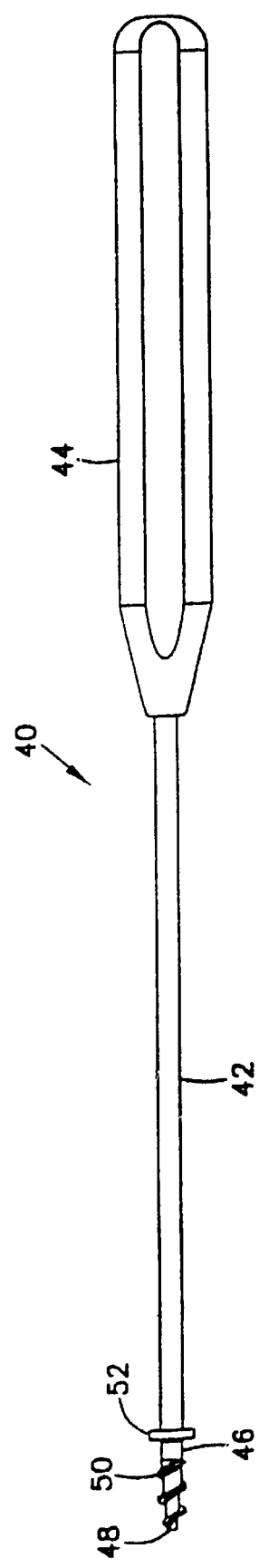
FIG. 5 is an elevation of a tap according to the present invention.
Figure 6:
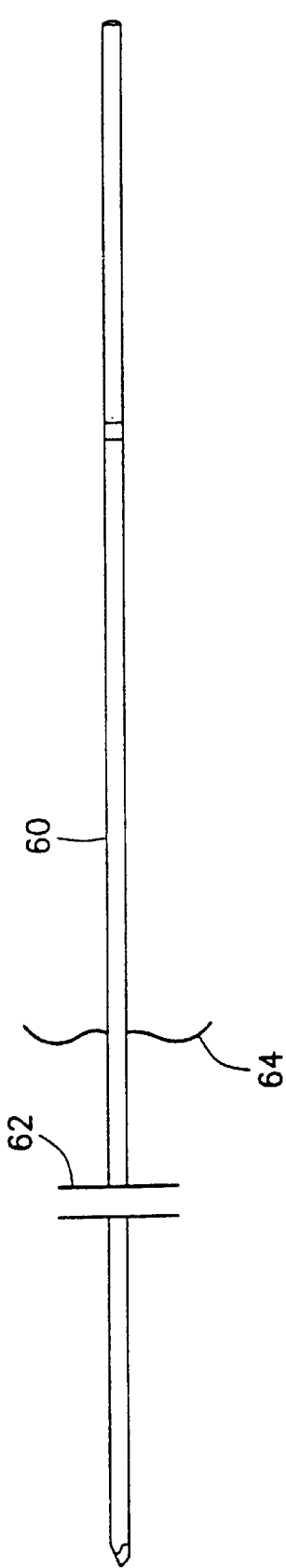
FIG. 6 is an elevation of a 1.0 mm guide wire used for installation of the headed anchor according to the present invention.
Figure 7:
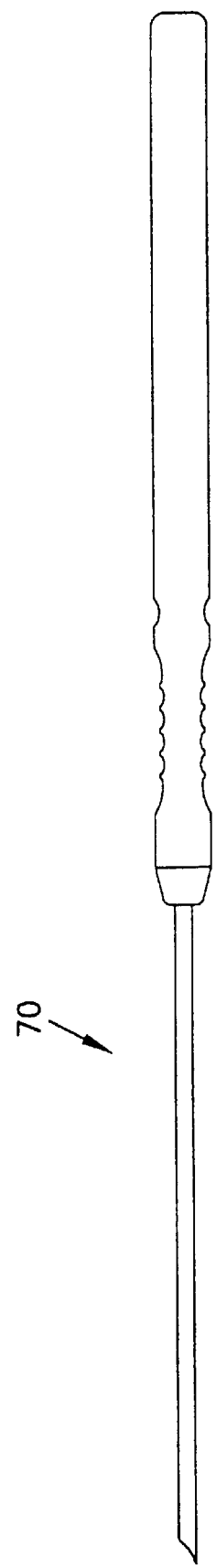
FIG. 7 is an elevation of a spear used to facilitate insertion of the guide wire according to the present invention.
Figure 9:
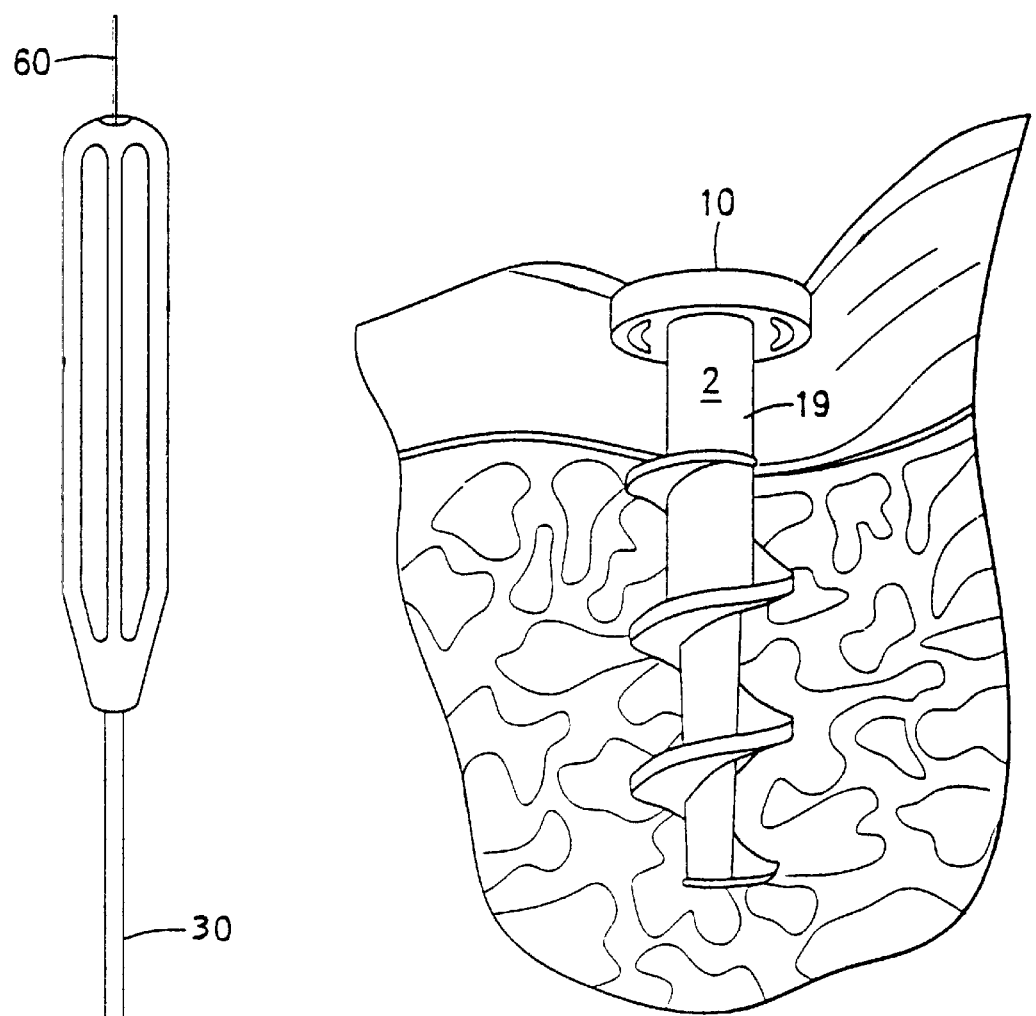
FIG. 9 is a schematic illustration of the tissue anchor of FIG. 1 installed through tissue and into bone.

FIG. 5 illustrates a cannulated tap 40 according to the present invention. The tap 40 includes a shaft 42 and a handle 44. Tap 40 has a tap head 46 provided on the distal end of the instrument. The tap head 46 has a trocar tip 48 and thread 50 for entering and tapping bone prior to insertion of the bioabsorbable corkscrew 2. A depth stop 52 engages the tissue to indicate an appropriate depth of insertion, as described below.

The configuration of the distal end of tap 50 is substantially similar to the configuration of the threaded portion of the anchor, described above. Advantageously, the outer diameter of the thread 50 on the tap is smaller than the outer diameter of the thread 6 on the anchor, typically by about 5%. Accordingly, the anchor thread 6 compresses bone tissue as it is installed by turning into the thread formed by the smaller tap thread 50. The forced fit enhances fixation strength. In a preferred embodiment, for example, the outer diameter of the anchor thread is 5.0 mm, and the outer diameter of the tap thread is 4.78 mm.

Figure 8:
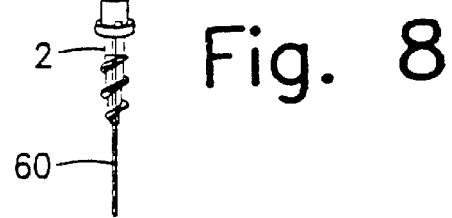
FIG. 8 is a perspective view of the tissue anchor of FIG. 1 assembled onto the driver of FIG. 4 and disposed over the guide wire of FIG. 6.

The present invention also provides an assembly of the headed bioabsorbable tissue anchor and the driver for installing the anchor. Referring to FIG. 8, the tissue anchor 2 is shown engaged on the end of driver 30. The assembly has been placed over a guide wire 60, as described below with respect to a preferred method of installation.

Indications for the headed bioabsorbable tissue anchor of the present invention include rotator cuff repair (full or partial tears), Bankart repair, SLAP lesion repair, biceps tenodesis, acromio-clavicular separation repair, deltoid repair, and capsular shift or capsulolabral reconstruction in the shoulder; lateral stabilization, medial stabilization, achilles tendon repair, hallux valgus reconstruction, midfoot reconstructions, and metatarsal ligament repair in the foot/ankle; medial collateral ligament repair, lateral collateral ligament, patellar tendon repair, posterior oblique ligament repair, and iliotibial band tenodesis in the knee; scapholunate ligament reconstruction, ulnar collateral ligament reconstruction, and radial collateral ligament reconstruction in the hand/wrist; and biceps tendon reattachment, tennis elbow repair, and ulnar or radial collateral ligament reconstruction in the elbow.

Referring to FIGS. 6–9, an illustrative, generalized method of securing soft tissue to bone using the headed bioabsorbable tissue anchor of the present invention received over a guide wire 60 is described as follows:
1. Prepare a bone bed site 62 by debriding the site with a high-speed bur or rasp.
2. Move the tissue 64 into the proper position apposing the prepared bone site 62.
3. Install a 1.0 mm guide wire 60 by advancing the guide wire through the tissue 64 and into the prepared bone bed 62 at an appropriate angle. See FIG. 6. Installation of the guide wire can be facilitated by inserting the guide wire through a cannulated spear 70 (FIG. 7) that has been used to pierce the tissue and firmly engage the bone surface with its pointed tip.
4. Place the cannulated tap 40 over the exposed guide wire 60 and advance by turning through the tissue and into the bone. The tap is advanced until the depth stop collar 52 depresses the tissue. Remove the tap by turning in the direction opposite to installation, while holding the guide wire in place.
5. Place the headed tissue anchor over the guide wire. Place the cannulated driver over the guide wire to engage the head of the anchor. See FIG. 8.
6. Advance the anchor by turning clockwise through the tissue and into the bone until the head of the implant depresses the tissue. See FIG. 9.
7. Repeat the installation steps, inserting additional anchors at other tissue locations for further fixation, as needed.
8. Remove the guide wire.

Accordingly, in a preferred method of rotator cuff repair, for example, the rotator cuff is retracted laterally and the spear 70 is inserted through the tendon. The guide wire 60 is advanced by turning into the debrided portion of the humerus. The tap, aligned over the guide wire, is turned through the tendon and into bone until the collar slightly depresses the tendon. During tap removal, a guide wire pusher (not shown) inserted into the back of the tap is used to keep the guide wire in place. The cannulated anchor is placed over the guide wire and atraumatically turned using a driver through the tendon into bone until the cuff is firmly apposed against bone. The guide wire is removed.

The broad apposition and compression of soft tissue to bone provided by the present invention speeds healing and provides a stronger soft tissue fixation, compared to sutures. Concurrently, the smooth upper surface of the anchor head 10 allows atraumatic articulation of the repaired joint. The cancellous thread provides enhanced thread purchase through the outer cortical bone layer. The anchor of the present invention withstands up to 90 pounds of pull-out force prior to failure. In addition, the PLA copolymer (PLDLA) material has a high inherent viscosity, and in degradation studies the anchor retains 90% of its fixation strength after 12 weeks.

Referring to FIGS. 10–13, an alternative embodiment 100 of the headed bioabsorbable tissue anchor of the present invention is shown. Anchor 100 is similar to the first embodiment, except that driver engagement has been enhanced, as follows: A body 104 is provided in the shape of a cannulated, tapered cylinder. A continuous thread 106 wraps around body 104 in a clockwise direction, as shown. The outer diameter of the thread remains substantially constant, while the inner diameter of the thread decreases distally, following the taper of the body 104. Accordingly, the surface area of the thread increases distally. The central core of body 104 preferably is circular in cross-section, and tapers from a maximum diameter near the proximal end to a minimum diameter toward the distal end.

Headed bioabsorbable tissue anchor 100 is provided at the proximal end of body 104 with a head 110. The anchor is provided with at least one opening for engaging a driver. Although many different drive coupling arrangements are possible, in the preferred alternative embodiment of the invention, equally spaced arcuate slots 112 are formed in the disk-shaped head to engage a driver described more fully below. The driver is used for delivery and installation of the anchor. Slots 112 formed in the head of the anchor preferably taper to enhance retention of the anchor on the distal end of the driver. The head 110 provides a broad area of tissue-to-bone contact, and has a smooth, low profile to minimize trauma to surrounding tissue.

At the distal tip 114, the anchor terminates in a flat end 116. The flat end is less likely than a pointed tip to break off and become a loose body within the patient. Cannula 118 is provided centrally. Preferably, the cannula is shaped to engage a driver for installation of the anchor by turning. Accordingly, the cannula could be a hexagon, a star, or provided with ridges, for example. A hexagonal shape is shown in the drawings. The cannula tapers to provide a secure fit with the driver.

The head 110 preferably is separated from the thread 106 by a smooth shank 119 that passes through and accommodates the tissue atraumatically upon insertion of the anchor into bone, as described more fully below.

A driver for the alternative embodiment of the present invention is similar to driver 40 described above, and includes a central, hexagonally shaped pin received in hexagonal cannula 118 of anchor 100. Accordingly, the driver engages both the hexagonal cannula 118 and the slots 112 to distribute the torsional load on the screw more evenly.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:
1. A headed bioabsorbable tissue anchor for attaching soft tissue to bone without using suture, the tissue anchor, comprising:
    a body formed of a bioabsorbable material, the body having a distal end and a proximal end;
    a continuous thread disposed in a spiral around the body and having an inner diameter, an outer diameter and a surface area, the surface area of the thread increasing from the proximal end to the distal end of the body;
    a disk-shaped head disposed on the proximal end of the body for engaging soft tissue and holding the soft tissue against bone without using suture, the head having an outer diameter greater than the outer diameter of the thread for compressing soft tissue to bone; and
    a coupling arrangement for engaging a driver for turning the anchor, the coupling arrangement comprising:
        (i) at least one slot that extends completely through the head of the anchor without extending into the body of the anchor for engaging a corresponding projection on the driver; and
        (ii) a cannula extending completely through the body of the tissue anchor and being shaped for receiving and engaging a central, correspondingly shaped pin of the driver.

2. The tissue anchor of claim 1, wherein the at least one slot comprises three arcuate slots for engaging corresponding projections on the driver.

3. The tissue anchor of claim 1, wherein the cannula tapers from the proximal end to the distal end to provide a secure fit with the pin of the driver.

4. The tissue anchor of claim 1, wherein the thread has a thickness at an outer edge of the thread which increases proximally along a portion of the thread.

5. The tissue anchor of claim 1, wherein the outer diameter of the thread is at least twice the inner diameter of the thread along a portion of the thread.

6. The tissue anchor of claim 1, wherein the outer diameter of the thread is substantially constant from the proximal end to the distal end.

7. The tissue anchor of claim 1, wherein the body tapers from the proximal end to the distal end.

8. The tissue anchor of claim 1, wherein the distal end of the body terminates in a flat tip.

9. The tissue anchor of claim 1, wherein the tissue anchor is formed of a PLA co-polymer.

10. The tissue anchor of claim 9, wherein the PLA co-polymer comprises poly(L/D-lactide) acid.

11. A method of anchoring tissue to bone using the headed bioabsorbable tissue anchor of claim 1, the method comprising the steps of installing the anchor through the tissue by turning the anchor with a driver into a pre-tapped hole in bone.

12. The tissue anchor of claim 1, wherein the cannula of the tissue anchor has a hexagonal shape.

* * * * *